(12) United States Patent
Islam et al.

(10) Patent No.: US 11,856,845 B2
(45) Date of Patent: Dec. 26, 2023

(54) COMPOUND

(71) Applicant: Sumitomo Chemical Company Limited, Tokyo (JP)

(72) Inventors: Nazrul Islam, Cambourne (GB); William Tarran, Godmanchester (GB); Jean-Benoit Giguere, Cambridge (GB)

(73) Assignee: Sumitomo Chemical Company Limited, Tokyo (JP)

( * ) Notice: Subject to any disclaimer, the term of this patent is extended or adjusted under 35 U.S.C. 154(b) by 534 days.

(21) Appl. No.: 16/955,756

(22) PCT Filed: Dec. 20, 2018

(86) PCT No.: PCT/GB2018/053722
§ 371 (c)(1),
(2) Date: Jun. 18, 2020

(87) PCT Pub. No.: WO2019/122900
PCT Pub. Date: Jun. 27, 2019

(65) Prior Publication Data
US 2020/0321532 A1    Oct. 8, 2020

(30) Foreign Application Priority Data
Dec. 21, 2017 (GB) ..................... 1721673

(51) Int. Cl.
| | | |
|---|---|---|
| *C07D 249/08* | (2006.01) | |
| *H10K 85/60* | (2023.01) | |
| H10K 50/17 | (2023.01) | |
| H10K 71/00 | (2023.01) | |
| H10K 71/30 | (2023.01) | |
| H10K 71/40 | (2023.01) | |

(52) U.S. Cl.
CPC ......... *H10K 85/654* (2023.02); *C07D 249/08* (2013.01); *H10K 85/631* (2023.02); *H10K 50/171* (2023.02); *H10K 71/00* (2023.02); *H10K 71/30* (2023.02); *H10K 71/40* (2023.02)

(58) Field of Classification Search
CPC ........................ C07D 249/08; H01L 51/0067
See application file for complete search history.

(56) References Cited

U.S. PATENT DOCUMENTS

| | | |
|---|---|---|
| 3,278,545 A | 10/1966 | Huisgen et al. |
| 2012/0205645 A1 | 8/2012 | Fuchs et al. |

FOREIGN PATENT DOCUMENTS

| | | |
|---|---|---|
| CA | 2340279 A1 | 12/2000 |
| FR | 2332708 A1 | 6/1977 |
| NL | 7613137 A | 5/1977 |
| WO | WO 00/78142 A3 | 12/2000 |
| WO | WO 2010/025558 A8 | 3/2010 |

OTHER PUBLICATIONS

Cheung, et al. Acta Crystallographica, Secition C: Crystal Structure Communications (1992); C48 (2), 342-4 (abstract); retrieved from STN; Accession No. 1992:140650.*
Combined Search and Examination Report for UK Application No. GB1721673.0, dated Oct. 5, 2018.
International Search Report and Written Opinion for Internatinal Application No. PCT/GB2018/053722, dated Jul. 2, 2019.
Booth et al., The synthesis and some reactions of N-methylnitrilium trifluoromethanesulphonate salts. Journal of the Chemical Society, Chemical Communications. 1980. pp. 1151-1153. doi: 10.1039/c39800001151.
Lee et al., Reactions of Nitrilium Salts. I. With Sodium and Dimethylammonium Azide. Journal of Organic Chemistry. 1972;37(3):343-347. doi:10.1021/jo00968a001.

* cited by examiner

*Primary Examiner* — Shawquia Jackson
(74) *Attorney, Agent, or Firm* — Wolf, Greenfield & Sacks, P.C.

(57) ABSTRACT

Compound A compound of formula (I): (I) wherein $R^1$ and $R^2$ are each independently a linear, branched or cyclic $C_{1-20}$alkyl group; and $Ar^1$ and $Ar^2$ are each independently an aromatic or heteroaromatic group which is unsubstituted or substituted with one or more substituents. The compound may be used in n-doping of an organic semiconductor. Such an n-doped organic semiconductor may be used in an organic electronic device, for example an electron injection layer of an organic light-emitting device.

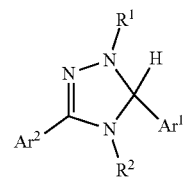

19 Claims, 3 Drawing Sheets

COMPOUND

RELATED APPLICATIONS

This Application is a national stage filing under 35 U.S.C. § 371 of international PCT application no. PCT/GB2018/053722, filed Dec. 20, 2018, which claims priority to United Kingdom patent application no. GB 1721673.0, filed Dec. 21, 2017, each of which is incorporated herein by reference in its entirety.

FIELD OF THE INVENTION

The invention relates to compositions and formulations for forming n-doped organic semiconductors, methods of forming n-doped organic semiconductors and devices containing n-doped organic semiconductors.

BACKGROUND OF THE INVENTION

Electronic devices containing active organic materials are known for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An organic light-emitting device has a substrate carrying an anode, a cathode and an organic light-emitting layer containing a light-emitting material between the anode and cathode.

In operation, holes are injected into the device through the anode and electrons are injected through the cathode. Holes in the highest occupied molecular orbital (HOMO) and electrons in the lowest unoccupied molecular orbital (LUMO) of the light-emitting material combine to form an exciton that releases its energy as light.

Cathodes include a single layer of metal such as aluminium, a bilayer of calcium and aluminium as disclosed in WO 98/10621; and a bilayer of a layer of an alkali or alkali earth compound and a layer of aluminium as disclosed in L. S. Hung, C. W. Tang, and M. G. Mason, Appl. Phys. Lett. 70, 152 (1997).

An electron-transporting or electron-injecting layer may be provided between the cathode and the light-emitting layer.

Bao et al, "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852-8853 discloses doping of [6,6]-phenyl $C_{61}$ butyric acid methyl ester (PCBM) by mixing (4-(1,3-dimethyl-2,3-dihydro-1H-benzoimidazol-2-yl)phenyl)dimethylamine (N-DMBI) with PCBM and activating the N-DMBI by heating.

US 2014/070178 discloses an OLED having a cathode disposed on a substrate and an electron-transporting layer formed by thermal treatment of an electron-transporting material and N-DMBI. It is disclosed that a radical formed on thermal treatment of N-DMBI may be an n-dopant.

U.S. Pat. No. 8,920,944 discloses n-dopant precursors for doping organic semiconductive materials.

Naab et al, "Mechanistic Study on the Solution-Phase n-Doping of 1,3-Dimethyl-2-aryl-2,3-dihydro-1H-benzoimidazole Derivatives", J. Am. Chem. Soc. 2013, 135, 15018-15025 discloses that n-doping may occur by a hydride transfer pathway or an electron transfer pathway.

EP 0749965 discloses synthesis of 1,2,4-triazoles of formula (Ib):

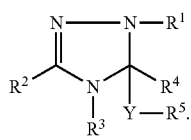

wherein Y is O or S and R5 is an organic residue.

Huisgen et al, Chemische Berichte, 97(4), 1085-95; 1964 discloses a compound of formula:

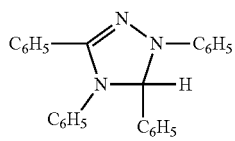

Warnhoff et al, Synthesis, (10), 876-9; 1987 discloses a compound of formula:

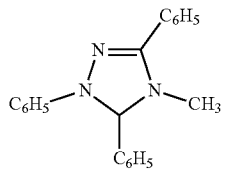

It is an object of the invention to provide stable compounds, in particular compounds having high stability in solution, which can be used to n-dope an organic semiconductor.

SUMMARY OF THE INVENTION

The present inventors have identified compounds which can be used to n-dope organic semiconductors.

Accordingly, in a first aspect the invention provides a compound of formula (I):

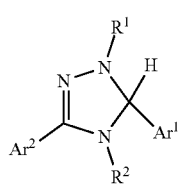

wherein $R^1$ and $R^2$ are each independently a linear, branched or cyclic $C_{1-20}$ alkyl group, more preferably a $C_{1-6}$ alkyl group, most preferably methyl; and $Ar^1$ and $Ar^2$ are each independently an aromatic or heteroaromatic group which is unsubstituted or substituted with one or more substituents.

In a second aspect the invention provides a composition comprising an organic semiconductor and a compound according to the first aspect.

In a third aspect the invention provides a formulation comprising a compound according to the first aspect and at least one solvent.

In a fourth aspect the invention provides a charge transfer salt formed by doping an organic semiconductor with an n-dopant formed from a compound of formula (I).

In a fifth aspect the invention provides a method of forming a charge-transfer salt, the method comprising the step of activating a composition according the second aspect.

In a sixth aspect the invention provides an organic electronic device comprising a layer comprising a charge-transfer salt according to the fourth aspect.

In a seventh aspect the invention provides a method of forming a layer of an organic electronic device comprising the step of depositing a layer of a composition according to the second aspect and activating the composition to cause n-doping of the organic semiconductor.

In an eight aspect the invention provides a composition comprising a compound of formula (II) and an organic semiconductor:

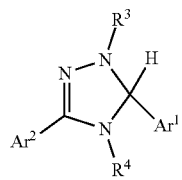

(II)

wherein $R^3$ and $R^4$ are each independently a substituent; and $Ar^1$ and $Ar^2$ are each independently an aromatic or heteroaromatic group which is unsubstituted or substituted with one or more substituents.

The invention provides a formulation comprising a composition according to the eighth aspect and at least one solvent.

The invention provides a charge transfer salt formed by doping the organic semiconductor of the eighth aspect with an n-dopant formed from the compound of formula (II).

The invention provides a method of forming a charge-transfer salt, the method comprising the step of activating the composition according the eighth aspect.

The invention provides an organic electronic device comprising a layer comprising a charge-transfer salt formed by activating the composition according the eighth aspect.

The invention provides a method of forming a layer of an organic electronic device comprising the step of depositing a layer of a composition according to the eighth aspect and activating the composition to cause n-doping of the organic semiconductor.

DESCRIPTION OF THE DRAWINGS

The invention will now be described in more detail with reference to the drawings in which.

DETAILED DESCRIPTION OF THE INVENTION

Figure 1:
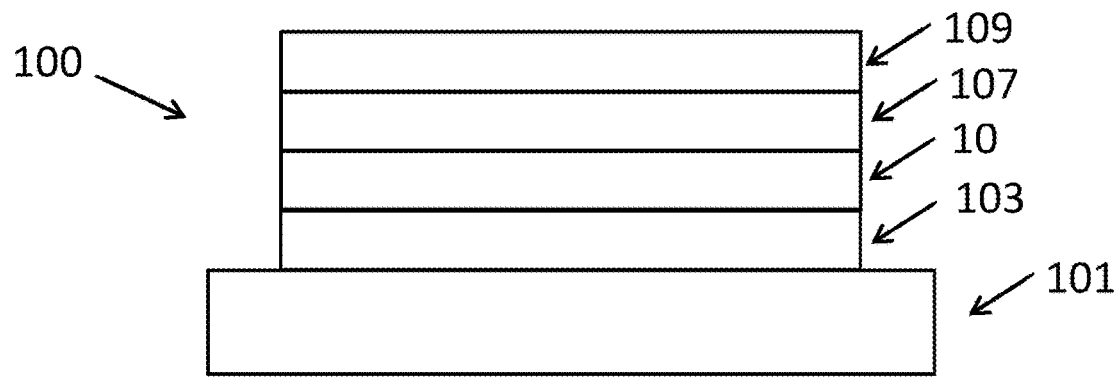
FIG. 1 illustrates schematically an OLED according to an embodiment of the invention.

Compounds of formula (I) are provided:

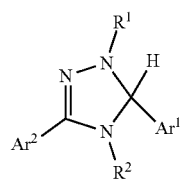

(I)

wherein $R^1$ and $R^2$ are each independently a linear, branched or cyclic $C_{1-20}$ alkyl group; and $Ar^1$ and $Ar^2$ are each independently an aromatic or heteroaromatic group which is unsubstituted or substituted with one or more substituents.

Compounds of formula (I) may be used in n-doping of organic semiconductors.

In other embodiments, the compound used in n-doping of an organic semiconductor has formula (II):

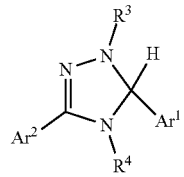

(II)

wherein $R^3$ and $R^4$ are each independently a substituent; and $Ar^1$ and $Ar^2$ are each independently an aromatic or heteroaromatic group which is unsubstituted or substituted with one or more substituents.

Optionally, $R^3$ and $R^4$ are each independently selected from the group consisting of a linear, branched or cyclic $C_{1-20}$ alkyl group; and an aromatic or heteroaromatic group which is unsubstituted or substituted with one or more substituents. In the case where $R^3$ or $R^4$ is an aromatic or heteroaromatic group, it may be selected from groups $Ar^1$ as described herein and is preferably phenyl which may be unsubstituted or substituted with one or more ionic or non-ionic substituents as described below. Optionally, one of $R^3$ and $R^4$ is an unsubstituted or substituted aromatic or heteroaromatic group and the other of $R^3$ and $R^4$ is a $C_{1-20}$ alkyl group.

Preferably, there is little or no spontaneous n-doping of an organic semiconductor upon contact with a compound of formula (I) or (II) at 25° C. Preferably, the extent of n-doping is increased upon activation of a composition of the compound of formula (I) or (II) and an organic semiconductor, for example by heating or irradiation of the composition.

Optionally, the compound of formula (I) or (II) has a HOMO level that is the same as or, preferably, deeper (further from vacuum level) than the LUMO level of the organic semiconductor, optionally at least 1 eV or 1.5 eV deeper than the LUMO level of the organic semiconductor.

Preferably, the compound of formula (I) or (II) has a singly occupied molecular orbital (SOMO) level that is within 0.3 eV of the LUMO of the organic semiconductor.

Substituents of the compound of formula (I) or (II) may be selected according to a desired solubility of the compound and or a desired energy level, for example HOMO or LUMO level, of the compound.

Optionally, $Ar^1$ and $Ar^2$ are each a $C_{6-20}$ aromatic group, preferably phenyl. $Ar^1$ and $Ar^2$ may each independently be unsubstituted or substituted with one or more substituents.

Substituents of $Ar^1$ and $Ar^2$ may independently in each occurrence be selected from non-ionic and ionic substituents.

$Ar^1$ and $Ar^2$ may be substituted with one or more non-ionic substituents wherein each is independently selected from the group consisting of branched, linear or cyclic $C_{1-12}$ alkyl wherein one or more non-adjacent, non-terminal C atoms of the $C_{1-12}$ alkyl group may be replaced with O, S, $NR^5$, C=O or COO wherein $R^5$ is a $C_{1-12}$ hydrocarbyl group. Preferred non-ionic substituents of $Ar^1$ and $Ar^2$ are $N(R^5)_2$ and $OR^5$.

Hydrocarbyl groups as described anywhere herein are preferably groups consisting of one or both of alkyl and phenyl groups, more preferably groups selected from $C_{1-12}$ alkyl; unsubstituted phenyl; and phenyl substituted with one or more $C_{1-6}$ alkyl groups.

$Ar^1$ and $Ar^2$ may be substituted with one or more ionic substituents selected from substituents of formula (III):

—(Sp$^1$)p-(A)q    (III)

wherein $Sp^1$ is a spacer group; A is an anion or cation; p is 0 or 1; q is 1 if p is 0; and q is at least 1, preferably 1, if p is 1, the compound of formula (I) or (II) further comprising one or more counterions B to balance the charge of the one or more anions or cations A.

Optionally, $Sp^1$ is selected from:

$C_{1-10}$ alkylene wherein one or more non-adjacent C atoms may be replace with O, S, C=O, COO or phenylene; and arylene or heteroarylene, preferably phenylene, that may be unsubstituted or substituted with one or more $C_{1-20}$ alkyl groups wherein one or more non-adjacent C atoms of the $C_{1-20}$ alkyl groups may be replaced with O, S, C=O or COO.

"$C_{1-10}$ alkylene" as used herein means a divalent carbon atom or divalent alkyl chain.

Optionally, arylene or heteroarylene groups of $Sp^1$ are selected from phenylene and 5 or 6 membered heteroarylene groups. Substituents of arylene or heteroarylene groups of $Sp^1$ are optionally selected from $C_{1-20}$ alkyl, optionally $C_{1-12}$ alkyl wherein one or more non-adjacent C atoms may be replaced with O, S, C=O or COO, preferably O.

A of formula (III) and B may have the same valency, with a counterion B balancing the charge of each A of formula (III).

Anion or cation A may be monovalent or polyvalent.

Preferably, A and B are each monovalent.

In another embodiment, the compound of formula (I) or (II) may comprise a plurality of anions or cations A, preferably monovalent anions or cations A, wherein the charge of two or more anions or cations A is balanced by a single, polyvalent counterion B. Optionally, the compound of formula (I) or (II) comprises one or more di- or trivalent cations B.

Exemplary anions A may be selected from, without limitation, sulfonate and —COO$^-$. A preferred anion A is —COO$^-$.

Exemplary cations A may be selected from organic or inorganic cations including, without limitation —N(R$^{11}$)$_3^+$; —P(R$^{11}$)$_3^+$; S(R$^{11}$)$_2^+$; or a heteroaromatic cation, optionally a heteroaromatic cation comprising or consisting of C and N atoms optionally pyridinium or imidazolium wherein R$^{11}$ in each occurrence is H or C$_{1-12}$ hydrocarbyl, optionally C$_{1-12}$ alkyl. A preferred cation A is —NR$^{11}_3{}^+$.

Cation B is optionally a metal cation, optionally Li$^+$, Na$^+$, K$^+$, Cs$^+$, preferably Cs$^+$, or an organic cation, optionally N(R$^{11}$)$_4^+$ such as tetraalkylammonium, or a heteroaromatic cation optionally ethylmethyl imidazolium or pyridinium. The size of the cation may affect the dopant strength of the n-dopant. Preferably, the cation is an organic cation or a metal cation from the third or higher periods of the Periodic Table, preferably fourth or higher periods, more preferably fifth or higher periods of the Periodic Table.

Anion B is optionally halide, optionally F—, Cl—, Br— or I—; hydroxide; a borate, optionally BF$_4^-$; a phosphate, optionally PF$_6^-$; a phosphinate; a phosphonate; an imide, optionally TFSI; or a sulfonate group, optionally mesylate, tosylate or sulfonate.

Exemplary compounds of formula (I) are:

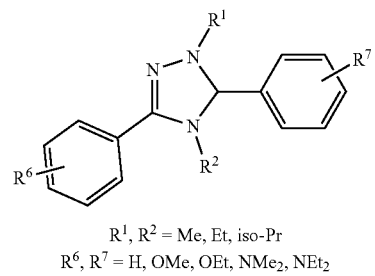

$R^1$, $R^2$ = Me, Et, iso-Pr
$R^6$, $R^7$ = H, OMe, OEt, NMe$_2$, NEt$_2$

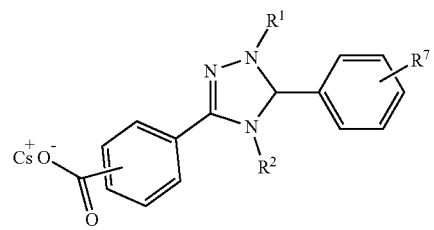

$R^1$, $R^2$ = Me, Et, iso-Pr
$R^7$ = H, OMe, OEt, NMe$_2$, NEt$_2$

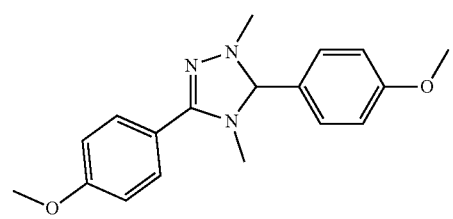

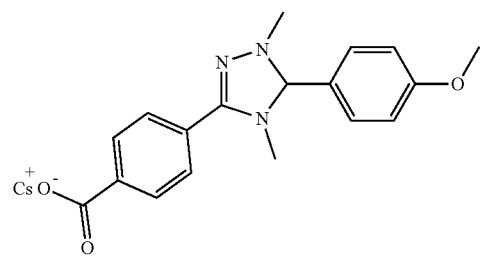

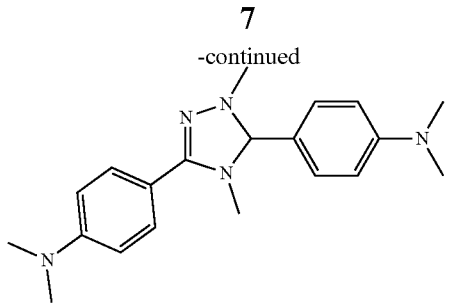

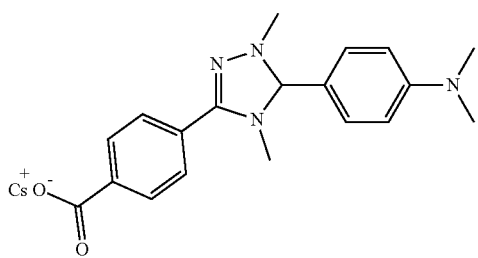

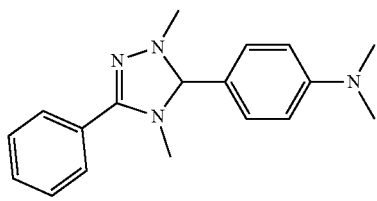

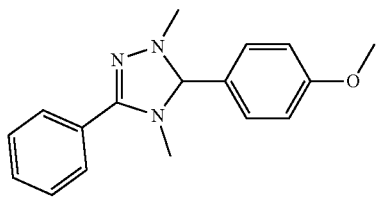

Organic Semiconductor

The organic semiconductor may be a polymeric or non-polymeric material. Optionally, the organic semiconductor is a polymer, more preferably a conjugated polymer.

The organic semiconductor may comprise a polar double or triple bond, optionally a bond selected from a C=N (imino) group, a nitrile group, a C=S group, an oxime group or a C=O group, optionally a keto, ester or carbonate group. Preferably, these polar double- or triple-bond groups are conjugated to a conjugated polymer backbone. These polar double- or triple-bond groups may be provided as substituents of a conjugated repeat unit or may be part of a conjugated repeat unit, for example fluorenone.

The organic semiconductor may be a polymer comprising electron-deficient heteroaromatic repeat units.

The organic semiconductor may comprise benzothiadiazole units. The benzothiadiazole units may be units of a polymer that is mixed with the polymer substituted with an n-dopant or a repeat unit in the backbone of the polymer substituted with an n-dopant. A polymeric repeat unit may comprise or consist of repeat units of formula:

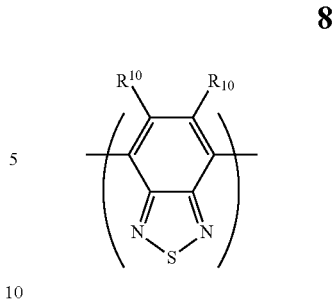

wherein $R^{10}$ in each occurrence is a substituent, optionally a substituent selected from alkyl, optionally $C_{1-20}$ alkyl, wherein one or more non-adjacent C atoms may be replaced with optionally substituted aryl or heteroaryl, O, S, C=O or —COO—, and one or more H atoms may be replaced with F.

A repeat unit comprising benzothiadiazole may have formula:

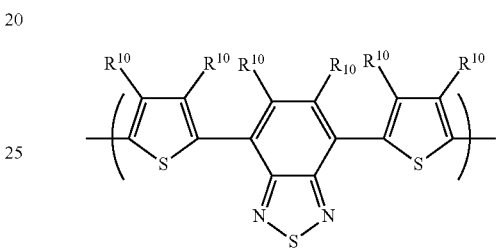

wherein $R^{10}$ is as described above.

The organic semiconductor may be a polymer comprising an unsubstituted or substituted $C_{1-20}$ arylene repeat unit.

Arylene repeat units include, without limitation, fluorene, phenylene, naphthalene, anthracene, indenofluorene, phenanthrene and dihydrophenanthrene repeat units, each of which may be unsubstituted substituted with one or more substituents.

Arylene repeat units may be selected from repeat units of formulae (IX)-(XII), each of which may be unsubstituted or substituted with one or more substituents:

(IX)

(X)

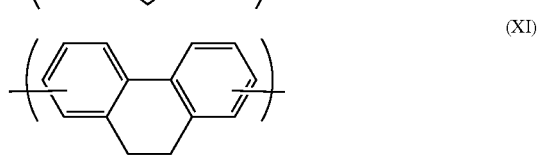
(XI)

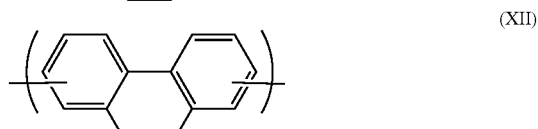
(XII)

Repeat units of formulae (IX)-(XII) may have formulae (IXa)-(XIIa) respectively:

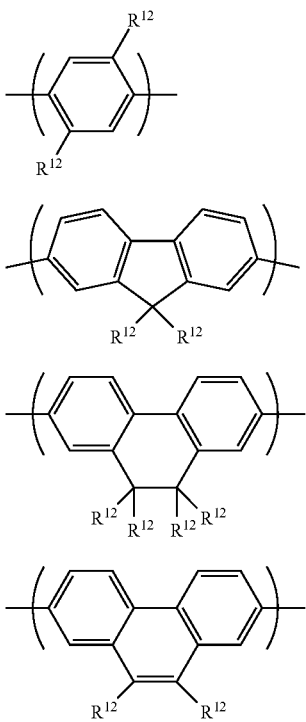

(IXa)

(Xa)

(XIa)

(XIIa)

wherein $R^{12}$ in each occurrence is a substituent. Optionally, substituents $R^{12}$ are selected from the group consisting of:

$C_{1-20}$ alkyl;

—$(Ar^2)_t$, wherein $Ar^2$ in each occurrence is an aromatic or heteroaromatic group, preferably, phenyl, which is unsubstituted or substituted with one or more substituents and t is at least 1, optionally 1, 2 or 3;

ionic substituents; and electron-withdrawing substituents, optionally cyano.

Preferred substituents include, without limitation, $C_{1-20}$ hydrocarbyl groups; ionic substituents; and electron-withdrawing substituents, optionally cyano.

Exemplary anionic substituents comprise formula —COO⁻ with a suitable metal or organic cation. Exemplary metal cations are alkali metal cations, preferably Cs+. Exemplary organic cations are ammonium, optionally tetraalkylammonium, ethylmethyl, imidazolium and pyridinium.

A polymer comprising ester substituents may be converted to a polymer comprising substituents formula —COO⁻M+. The conversion may be as described in WO 2012/133229, the contents of which are incorporated herein by reference.

The polymer may comprise an electron-accepting unit in its backbone, for example a repeat unit comprising benzothiadiazole; an arylene repeat unit substituted with one or more electron-withdrawing groups; or a repeat unit comprising a polar double or triple bond. A polymer comprising an electron-deficient arylene or heteroarylene repeat unit or may be a copolymer comprising one or more co-repeat units. The co-repeat units may be selected from arylene co-repeat units that are not substituted with an electron-withdrawing group and are optionally unsubstituted or substituted with one or more substituents selected from $C_{1-40}$ hydrocarbyl groups and ionic groups. Ionic groups may be as described with respect to formula (III).

The organic semiconductor:compound of formula (I) or (II) weight ratio is optionally in the range 99:1-10:90.

Optionally the compound of formula (I) or (II):organic semiconductor molar ratio is greater than 50:50 in which case not all of the compound of formula (I) or (II) may be consumed in doping of the organic semiconductor.

Polymers as described anywhere herein, including polymers substituted with an n-dopant and semiconductor polymers, suitably have a polystyrene-equivalent number-average molecular weight (Mn) measured by gel permeation chromatography in the range of about $1 \times 10^3$ to $1 \times 10^8$, and preferably $1 \times 10^3$ to $5 \times 10^6$. The polystyrene-equivalent weight-average molecular weight (Mw) of polymers described anywhere herein may be $1 \times 10^3$ to $1 \times 10^8$, and preferably $1 \times 10^4$ to $1 \times 10^7$.

Polymers as described anywhere herein are suitably amorphous polymers.

Applications

An organic electronic device may contain a layer comprising or consisting of an n-doped organic semiconductor formed from a compound of formula (I) or (II) and an organic semiconductor.

The layer may be, without limitation, an electron injection layer of an organic light-emitting device; an electron-extraction layer of an organic photovoltaic device or organic photodetector; an auxiliary electrode layer of an n-type organic thin film transistor; or an n-type semiconductor in a thermoelectric generator.

Preferably, the layer is an electron injection layer of an organic light-emitting device.

FIG. 1, which is not drawn to any scale, illustrates an OLED 100 according to an embodiment supported on a substrate 101, for example a glass or plastic substrate. The OLED 100 comprises an anode 103, a light-emitting layer 105, an electron-injecting layer 107 and a cathode 109.

The anode 103 may be single layer of conductive material or may be formed from two or more conductive layers. Anode 103 may be a transparent anode, for example a layer of indium-tin oxide. A transparent anode 103 and a transparent substrate 101 may be used such that light is emitted through the substrate. The anode may be opaque, in which case the substrate 101 may be opaque or transparent, and light may be emitted through a transparent cathode 109.

Light-emitting layer 105 contains at least one light-emitting material. Light-emitting material 105 may consist of a single light-emitting compound or may be a mixture of more than one compound, optionally a host doped with one or more light-emitting dopants. Light-emitting layer 105 may contain at least one light-emitting material that emits phosphorescent light when the device is in operation, or at least one light-emitting material that emits fluorescent light when the device is in operation. Light-emitting layer 105 may contain at least one phosphorescent light-emitting material and at least one fluorescent light-emitting material.

Electron-injecting layer 107 comprises or consists of a charge-transfer complex formed from an organic semiconductor and a compound of formula (I) or (II).

Cathode 109 is formed of at least one layer, optionally two or more layers, for injection of electrons into the device.

Preferably, the electron-injecting layer 107 is in contact with organic light-emitting layer 105. Preferably, the film comprising the organic semiconductor and n-dopant is formed directly on organic light-emitting layer 105.

Preferably, the organic semiconductor has a LUMO that is no more than about 1 eV, optionally less than 0.5 eV or 0.2 eV, deeper (i.e. further from vacuum) than a LUMO of a material of the light-emitting layer, which may be a LUMO of a light-emitting material or a LUMO of a host material if the light-emitting layer comprises a mixture of a host material and a light-emitting material. Optionally, the doped organic semiconductor has a work function that is about the same as a LUMO of a material of the light-emitting layer. Optionally, the organic semiconductor has a LUMO of less (i.e. closer to vacuum) than 3.0 eV from vacuum level, optionally around 2.1 to 2.8 eV from vacuum level. Preferably, the organic semiconductor has a LUMO level of up to 2.2 or 2.3 eV below the vacuum level.

Preferably, the cathode 109 is in contact with the electron-injecting layer 107.

Preferably, during manufacture of the device, the cathode is formed directly on the layer comprising a composition of the organic semiconductor and the compound of formula (I) or (II), and the composition is activated after formation of the cathode.

The OLED 100 may be a display, optionally a full-colour display wherein the light-emitting layer 105 comprises pixels comprising red, green and blue subpixels.

The OLED 100 may be a white-emitting OLED. White-emitting OLEDs as described herein may have a CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K. A white-emitting OLED may contain a plurality of light-emitting materials, preferably red, green and blue light-emitting materials, more preferably red, green and blue phosphorescent light-emitting materials, that combine to produce white light. The light-emitting materials may all be provided in light-emitting layer 105, or one or more additional light-emitting layers may be provided.

A red light-emitting material may have a photoluminescence spectrum with a peak in the range of about more than 550 up to about 700 nm, optionally in the range of about more than 550 nm or more than 580 nm up to about 630 nm or 650 nm.

A green light-emitting material may have a photoluminescence spectrum with a peak in the range of about more than 490 nm up to about 550 nm, optionally from about 500 nm, 510 nm or 520 nm up to about 550 nm.

A blue light-emitting material may have a photoluminescence spectrum with a peak in the range of up to about 490 nm, optionally about 450-490 nm.

The photoluminescence spectrum of a material may be measured by casting 5 wt % of the material in a PMMA film onto a quartz substrate and measuring in a nitrogen environment using apparatus C9920-02 supplied by Hamamatsu.

The OLED 100 may contain one or more further layers between the anode 103 and the cathode 109, for example one or more charge-transporting, charge-blocking or charge-injecting layers. Preferably, the device comprises a hole-injection layer comprising a conducting material between the anode and the light emitting layer 105. Preferably, the device comprises a hole-transporting layer comprising a semiconducting hole-transporting material between the anode 103 and the light emitting layer 105.

The OLED 100 may contain one or more light-emitting layers.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12 1737-1750, 2000, WO 99/54385, WO 00/46321 and WO 2012/104579, the contents of which are incorporated herein by reference. Light-emitting layer 107 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission. A plurality of light-emitting layers may together produce white light.

A fluorescent light-emitting layer may consist of a light-emitting material alone or may further comprise one or more further materials mixed with the light-emitting material. Exemplary further materials may be selected from hole-transporting materials; electron-transporting materials and triplet-accepting materials, for example a triplet-accepting polymer as described in WO 2013/114118, the contents of which are incorporated herein by reference.

The cathode may comprise one or more layers. Preferably, the cathode comprises or consists of a layer in contact with the electron injecting layer that comprises or consists of one or more conductive materials. Exemplary conductive materials are metals, preferably metals having a work function of at least 4 eV, optionally aluminium, copper, silver or gold or iron. Exemplary non-metallic conductive materials include conductive metal oxides, for example indium tin oxide and indium zinc oxide, graphite and graphene. Work functions of metals are as given in the CRC Handbook of Chemistry and Physics, 12-114, $87^{th}$ Edition, published by CRC Press, edited by David R. Lide. If more than one value is given for a metal then the first listed value applies.

The cathode may be opaque or transparent. Transparent cathodes are particularly advantageous for active matrix devices because emission through a transparent anode in such devices is at least partially blocked by drive circuitry located underneath the emissive pixels.

It will be appreciated that a transparent cathode device need not have a transparent anode (unless a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

A hole transporting layer may be provided between the anode 103 and the light-emitting layer 105.

The hole-transporting layer may be cross-linked, particularly if an overlying layer is deposited from a solution. The crosslinkable group used for this crosslinking may be a crosslinkable group comprising a reactive double bond such and a vinyl or acrylate group, or a benzocyclobutane group. Crosslinking may be performed by thermal treatment, preferably at a temperature of less than about 250° C., optionally in the range of about 100-250° C.

A hole transporting layer may comprise or may consist of a hole-transporting polymer, which may be a homopolymer or copolymer comprising two or more different repeat units. The hole-transporting polymer may be conjugated or non-conjugated. Exemplary conjugated hole-transporting polymers are polymers comprising arylene repeat units, e.g. fluorene repeat units, and arylamine repeat units, for example as described in WO 99/54385, WO 2005/049546 and WO2013/108022, the contents of which are incorporated herein by reference. Conjugated hole-transporting copolymers comprising arylamine repeat units may have one or more co-repeat units selected from arylene repeat units, for example one or more repeat units selected from fluorene, phenylene, phenanthrene naphthalene and anthracene repeat units, each of which may independently be unsubstituted or substituted with one or more substituents, optionally one or more $C_{1-40}$ hydrocarbyl substituents.

If present, a hole transporting layer located between the anode and the light-emitting layer 105 preferably has a HOMO level of 5.5 eV or shallower (closer to vacuum), more preferably around 4.8-5.5 eV or 5.1-5.3 eV as measured by square wave voltammetry. The HOMO level of the hole transport layer may be selected so as to be within 0.2 eV, optionally within 0.1 eV, of an adjacent layer in order to provide a small barrier to hole transport between these layers.

Preferably a hole-transporting layer, more preferably a crosslinked hole-transporting layer, is adjacent to the light-emitting layer 105.

A hole-transporting layer may consist essentially of a hole-transporting material or may comprise one or more further materials. A light-emitting material, optionally a phosphorescent material, may be provided in the hole-transporting layer.

A phosphorescent material may be covalently bound to a hole-transporting polymer as a repeat unit in the polymer backbone, as an end-group of the polymer, or as a side-chain of the polymer. If the phosphorescent material is provided in a side-chain then it may be directly bound to a repeat unit in the backbone of the polymer or it may be spaced apart from the polymer backbone by a spacer group. Exemplary spacer groups include $C_{1-20}$ alkyl and aryl-$C_{1-20}$ alkyl, for example phenyl-$C_{1-20}$ alkyl. One or more carbon atoms of an alkyl group of a spacer group may be replaced with O, S, C=O or COO.

Emission from a light-emitting hole-transporting layer and emission from light-emitting layer 105 may combine to produce white light.

A conductive hole injection layer, which may be formed from a conductive organic or inorganic material, may be provided between the anode 103 and the light-emitting layer 105 of an OLED as illustrated in FIG. 1 to assist hole injection from the anode into the layer or layers of semi-conducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Activation n-Doping may be effected by activation of a layer containing a compound of formula (I) or (II) and an organic semiconductor, for example by heating and/or irradiation of the layer. Activation may be by excitation of the n-dopant and/or the organic semiconductor.

Without wishing to be bound by any theory, activation may result in formation of a radical cation which is capable of n-doping the organic semiconductor.

Preferably, n-doping is effected after formation of a device comprising a layer containing an organic semiconductor and a compound of formula (I) or (II). Activation may be before or after encapsulation of the device.

Exemplary activation methods are thermal treatment and irradiation.

Optionally, thermal treatment is at a temperature in the range 80° C. to 170° C., preferably 120° C. to 170° C. or 130° C. to 160° C.

Thermal treatment and irradiation as described herein may be used together.

For irradiation, any wavelength of light may be used, for example a wavelength having a peak in the range of about 200-700 nm. Optionally, the peak showing strongest absorption in the absorption spectrum of the organic semiconductor is in the range of 400-700 nm Preferably, the strongest absorption of the n-dopant is at a wavelength below 400 nm.

The light emitted from the light source suitably overlaps with an absorption feature, for example an absorption peak or shoulder, of the organic semiconductor's absorption spectrum. Optionally, the light emitted from the light source has a peak wavelength within 25 nm, 10 nm or 5 nm of an absorption maximum wavelength of the organic semiconductor, however it will be appreciated that a peak wavelength of the light need not coincide with an absorption maximum wavelength of the organic semiconductor.

Preferably, no more than 10% or no more than 5% of the light output of the electromagnetic radiation source is from radiation having a wavelength less than or equal to 400 nm, optionally less than or equal to 420 nm. Preferably, none of the light output has a wavelength of less than or equal to 400 nm, optionally less than or equal to 420 nm Inducing n-doping without exposure to short wavelength light, such as UV light, may avoid damage to the materials of the OLED.

Optionally, irradiation time is between 1 second and 1 hour, optionally between 1-30 minutes.

Any suitable electromagnetic radiation source may be used to irradiate the film including, without limitation, fluorescent tube, incandescent bulb and organic or inorganic LEDs. Optionally, the electromagnetic radiation source is an array of inorganic LEDs. The electromagnetic radiation source may produce radiation having one or more than one peak wavelengths. Preferably, the electromagnetic radiation source has a light output of at least 2000 mW, optionally at least 3000 mW, optionally at least 4000 mW.

The extent of doping may be controlled by one or more of: the organic semiconductor/n-dopant ratio; excitation temperature; the peak wavelength of the light; the duration of excitation; and the intensity of the light.

The n-doped organic semiconductor may be an extrinsic or degenerate semiconductor.

In manufacture of an organic electronic device, such as an OLED as described in FIG. 1, activation may take place during device formation or after the device has been formed. Preferably, activation to cause n-doping takes place after the device has been formed and encapsulated. The device may be manufactured in an environment in which little or no spontaneous doping occurs, for example a room temperature environment wherein the compound of formula (I) or (II) and organic semiconductor are exposed to little or no wavelengths of light that induce n-doping until after encapsulation of the device, for example an environment illuminated by light having a longer wavelength than that of the electromagnetic radiation source such as a clean room illuminated with yellow light.

In the case of an OLED as described in FIG. 1, a film 107 of the polymer substituted with the n-dopant and the organic semiconductor may be formed over organic light-emitting layer 105 and the cathode 109 may be formed over the film.

For activation by irradiation, the film may then irradiated through the anode 101, in the case of a device formed on a transparent substrate 101 and having a transparent anode 103, such as ITO, or the film may be irradiated through the cathode 109 in the case of a device with a transparent cathode. The wavelength used to induce n-doping may be selected to avoid wavelengths that are absorbed by layers of the device between the electromagnetic radiation source and the film.

Encapsulation

Organic electronic devices as described herein may be encapsulated to prevent ingress of moisture and oxygen. A composition of a compound of formula (I) or (II) and an organic semiconductor may be activated to n-dope the organic semiconductor before or after encapsulation of the device.

Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

The substrate on which the device is formed preferably has good barrier properties such that the substrate together with the encapsulant forms a barrier against ingress of moisture or oxygen. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

Formulation Processing

Compositions comprising a compound of formula (I) or (II) and the organic semiconductor may be deposited by any suitable technique including, without limitation, thermal evaporation and deposition from a formulation comprising the compound of formula (I) or (II) and the organic semiconductor dissolved or dispersed in one or more solvents. Deposition from a solution is preferred.

A layer comprising the composition of the organic semiconductor and compound of formula (I) or (II) may be formed by depositing a formulation as described herein in air.

One or more solvents a formulation as described herein may be a polar solvent, optionally a protic solvent, optionally water or an alcohol; dimethylsulfoxide; propylene carbonate; or 2-butanone. Exemplary alcohols include methanol ethanol, propanol, butoxyethanol and monofluoro-, polyfluoro- or perfluoro-alcohols, optionally 2,2,3,3,4,4,5,5-Octafluoro-1-pentanol.

Compounds of formula (I) or (II) and organic semiconductors substituted with one or more ionic substituents may have enhanced solubility in polar solvents as compared to compounds without such ionic substituents.

Particularly preferred solution deposition techniques including printing and coating techniques such spin-coating, inkjet printing and lithographic printing.

Coating methods are particularly suitable for devices wherein patterning of the light-emitting layer is unnecessary—for example for lighting applications or simple monochrome segmented displays.

Printing methods are particularly suitable for high information content displays, in particular full colour displays. A device may be inkjet printed by providing a patterned layer over the anode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, slot die coating, roll printing and screen printing.

If a composition as described herein is deposited from a formulation onto an underlying organic layer, such as an organic light-emitting layer 105, then the solvent or solvents of the formulation may be selected so as to avoid dissolution of the underlying organic layer, or the underlying layer may be crosslinked.

Preferably, light-emitting layer 105 is formed by depositing a solution in which the solvent is one or more non-polar solvent materials, optionally benzenes substituted with one or more substituents selected from $C_{1-12}$ alkyl and $C_{1-12}$ alkoxy groups, for example toluene, xylenes and methylanisoles, and mixtures thereof.

EXAMPLES

Measurements

HOMO and LUMO levels as described anywhere herein are as measured by square wave voltammetry.

Equipment:

CHI660D Electrochemical workstation with software (IJ Cambria Scientific Ltd))

CHI 104 3 mm Glassy Carbon Disk Working Electrode (IJ Cambria Scientific Ltd))

Platinum wire auxiliary electrode

Reference Electrode (Ag/AgCl) (Harvard Apparatus Ltd)

Chemicals

| | |
|---|---|
| Acetonitrile (Hi-dry anhydrous grade-ROMIL) | (Cell solution solvent) |
| Toluene (Hi-dry anhydrous grade) | (Sample preparation solvent) |
| Ferrocene-FLUKA | (Reference standard) |
| Tetrabutylammoniumhexafluorophosphate-FLUKA | (Cell solution salt) |

Sample Preparation

The acceptor polymers were spun as thin films (~20 nm) onto the working electrode; the dopant material was measured as a dilute solution (0.3 w %) in toluene.

Electrochemical Cell

The measurement cell contains the electrolyte, a glassy carbon working electrode onto which the sample is coated as a thin film, a platinum counter electrode, and an Ag/AgCl reference glass electrode. Ferrocene is added into the cell at the end of the experiment as reference material (LUMO (ferrocene)=−4.8 eV).

For measurement of SOMO of the activated for of compounds of formula (I) or (II) the voltage for the square wave sweep is started at +1.8V vs Ag/AgCl which causes oxidative decomposition to the final doping product. The SOMO energy is then observed as the potential is lowered upon reduction to the radical form. Measuring a reductive sweep starting at 0V vs Ag/AgCl gives no response within the solvent window as no active form is present.

Compound Example 1

Compound Example 1 was prepared according to the following reaction scheme:

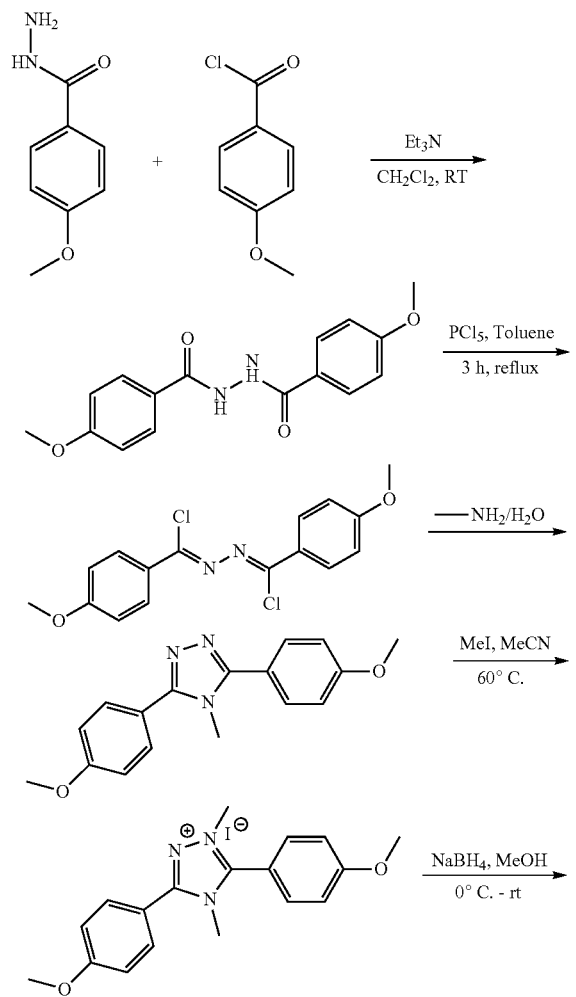

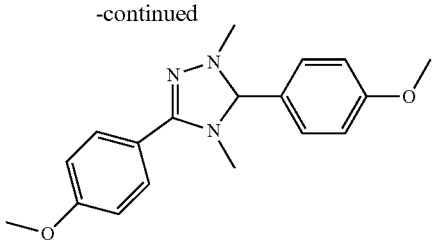

Compound Example 1

Synthesis of 4-methoxy-N'-(4-methoxybenzoyl) benzohydrazide

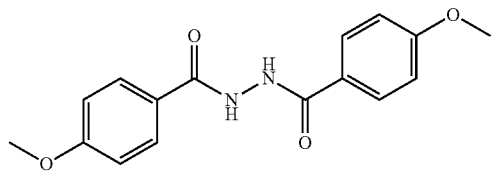

In an oven dried 500 ml three neck flask 4-methoxybenzohydrazide (5.06 g, 30.48 mmol) and 4-methoxybenzoyl chloride (5.2 g, 30.48) were taken. Dichloromethane (130 ml) was added and the resultant suspension was stirred for 5 min. A dichloromethane solution (20 ml) of trimethylamine (3.39 g, 4.6 ml, 33.53 mmol) was added into the reaction mixture dropwise. With addition of Et$_3$N a milky appearance was observed along with formation of mist. The reaction mixture was stirred at room temperature for 16 hours. LC-MS analysis showed mainly a peak having the desired product mass. The reaction was stopped and filtered through a filter paper under vacuum. The obtained white solid was washed with dichloromethane (50 ml×2) giving pure material, 8.3 g, 99.51% HPLC, 94% yield.

$^1$H-NMR (600 MHz, DMSO-d8): δ=10.2 (s, 2H), 8.13 (d, 2H), 7.95 (m, 2H), 7.02 (d, 2H), 3.25 (s, 6H).

Synthesis of N-chloro(4-methoxyphenyl)methylene)-4-methoxybenzohydrazonoyl Chloride

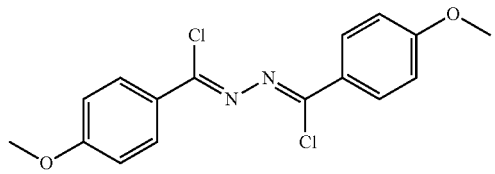

In a 250 ml three neck flask fitted with condenser, nitrogen inlet 4-methoxy-N'-(4-methoxybenzoyl)benzohydrazide (5.0 g, 16.65 mmol) was taken followed by addition of toluene (20 ml). Phosphorous pentachloride (7.97 g, 38.29 mmol, 2.3 equivalent) was added into the reaction flask in portion with stirring. The reaction mixture was heated to 120° C. for 3 hr during which a light green clear solution formed. The reaction mixture was cooled down to room temperature, toluene was distilled off and the reaction product was filtered under vacuum. The solid was collected and suspended in water (30 ml), stirred for 10 min then filtered. The obtained white solid was washed with water (50 ml) and dried in oven at 50° C. overnight, 3.5 g which was used for next step without further purification.

$^1$H-NMR (600 MHz, DMSO-d8): δ=7.78 (d, 4H), 6.69 (d, 4H), 4.02 (s, 6H).

Synthesis of 3,5-bis(4-methoxyphenyl)-4-methyl-4H-1,2,4-triazole

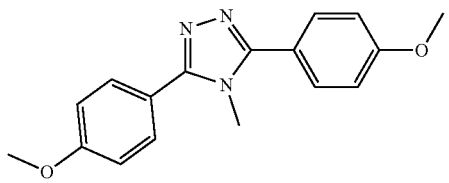

In a 100 ml three neck flask, fitted with a condenser and nitrogen inlet N-chloro(4-methoxyphenyl)methylene)-4-methoxybenzohydrazonoyl chloride (3.5 g, 10.38 mmol) was taken. A 40% aqueous solution of methylamine (35 ml) was added and stirred. The resultant suspension was heated to 80° C. for 16 hr. LC-MS shows the desired product mass. The reaction was cooled down to room temperature and filtered. The obtained white solid was purified by recrystallization from ethanol/toluene giving pure material, 2.2 g 71.8% yield, 99.6% HPLC.

$^1$H-NMR (600 MHz, CDCl3): δ=7.65 (d, 4H), 7.03 (d, 4H), 3.87 (s, 6H), 3.66 (s, 3H).

Synthesis of 3,5-bis(4-methoxyphenyl)-1,4-dimethyl-4H-1,2,4-triazol-1-ium Iodide

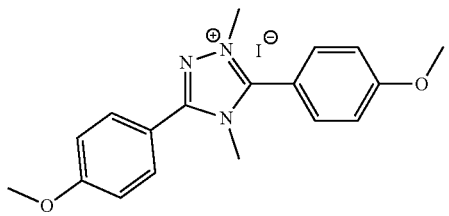

In a 500 ml three neck flask fitted with a condenser and nitrogen inlet 3,5-bis(4-methoxyphenyl)-4-methyl-4H-1,2,4-triazole (2.2 g, 7.45 mmol) was taken. Acetonitrile (100 ml) was added and stirred. Methyl iodide (2.6 g, 18.6 mmol, 2.5 equivalents) was added dropwise into the suspension and the reaction mixture was heated at 60° C. for 16 hours. While heating, within 1 hr a clear solution formed. The reaction was stopped, cooled down to room temperature and filtered through a filter paper. The filtrate was concentrated to dryness giving colourless flakes which were further purified by recrystallization from ethyl acetate/acetonitrile giving pure material, 1.4 g, 100% yield. The structure was confirmed by NMR and LC-MS analysis.

$^1$H-NMR (600 MHz, CDCl3): δ=8.07 (d, 2H), 7.89 (d, 2H), 7.17 (d, 2H), 7.05 (d, 2H), 4.01 (s, 3H), 3.91 (s, 3H), 3.87 (s, 3H), 3.83 (s, 3H).

Synthesis of 3,5-bis(4-methoxyphenyl)-1,4-dimethyl-4,5-dihydro-1H-1,2,4-triazole

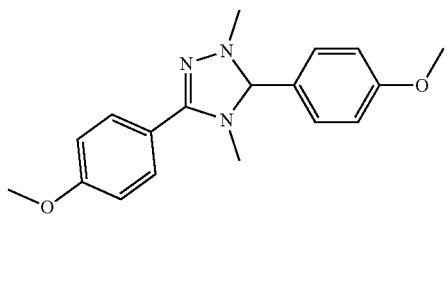

In an oven dried 100 ml flask 3,5-bis(4-methoxyphenyl)-1,4-dimethyl-4,5-dihydro-1H-1,2,4-triazole (1.5 g, 3.43 mmol) was taken under nitrogen. Anhydrous methanol (40 ml) was added and stirred. The reaction mixture was cooled down to 0° C. using a dry ice/acetone bath. Sodium borohydride (0.389 g, 10.29 mmol) was added in portions while maintaining internal temperature at 0° C. The reaction mixture was stirred at 0° C. for 30 minutes then allowed to warm up to room temperature and stirred for 1 hour. LC-MS showed the complete conversion of starting material into the desired product. The reaction was stopped and transferred into a separatory funnel and extracted with degassed ethyl acetate/water. The organic layer was washed successively with sodium thiosulfate and water. Evaporation of solvent gave a viscous liquid which was dissolved in dichloromethane (10 ml) and precipitated from pentane (100 ml). The solid was filtered followed by further purification by crystallisation from pentane. The material was dried under vacuum at room temperature, 0.570 g, 53% yield, 99.99% HPLC.

$^1$H-NMR (600 MHz, CDCl3): δ=7.52 (m, 4H), 6.93 (m, 4H), 4.51 (s, 1H), 3.84 (s, 3H), 3.82 (s, 3H), 2.66 (s, 3H), 2.51 (s, 3H).

Modelling Data

HOMO and SOMO levels of compounds shown in Table 1 were modelled.

Calculated redox potentials were obtained using Gaussian09 as described in *J. Phys. Chem. A* 2002, 106, 7407-7412. Geometries were optimised for the oxidised and reduced states, and frequency calculations performed to obtain free energy corrections to the state energies. Energy corrections for solvation in toluene were applied based on the SCF energy difference from single point SCRF calculations at the optimised geometries. Calculations were performed using the B3LYP functional and 6-31 g(d) basis set.

The modelled SOMO of the active form of compounds of formula (I) or (II) are shallower (closer to vacuum) than that of Comparative Compound 1.

TABLE 1
| Precursor Structure | Precursor HOMO (eV) | Active SOMO (eV) |
|---|---|---|
| Comparative Compound 1 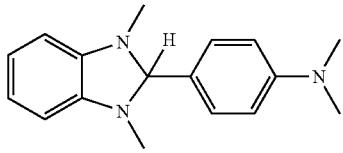 | −4.62 | −2.94 |
| Compound Example 1 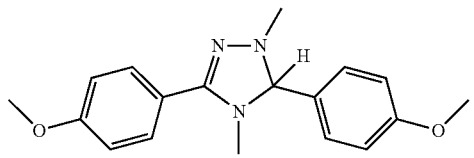 | −4.64 | −2.72 |
| 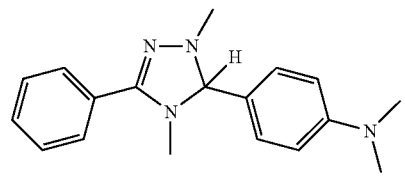 [SMILES: CN(C)c1ccc(C2N(C)N=C(c3ccccc3)N2C)cc1] | −4.66 | −2.64 |
| 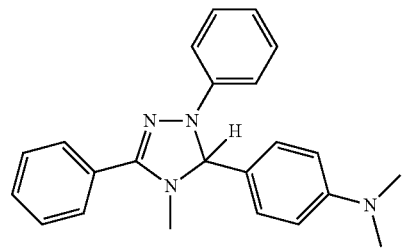 [SMILES: CN(C)c1ccc(C2N(C)C(c3ccccc3)=NN2c2ccccc2)cc1] | −4.73 | −2.86 |
| 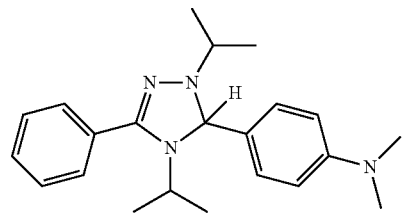 [SMILES: CC(C)N1N=C(c2ccccc2)N(C(C)C)C1c1ccc(N(C)C)cc1] | −4.46 | −2.53 |
| 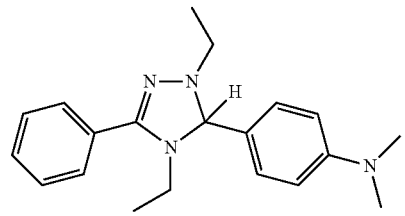 [SMILES: CCN1N=C(c2ccccc2)N(CC)C1c1ccc(N(C)C)cc1] | −4.57 | −2.50 |
| 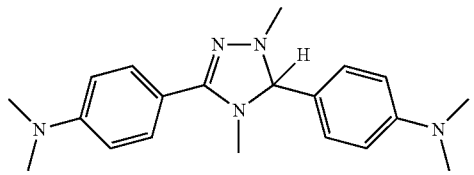 | −4.34 | −2.46 |

TABLE 1-continued

| Precursor Structure | Precursor HOMO (eV) | Active SOMO (eV) |
|---|---|---|
| (structure: CsO-C(=O)-C6H4-C(=N-N(CH3))-N(H)-CH-C6H4-C(=O)-OCs) | −4.23 | −2.36 |

Formulation Example

Formulations as set out in Table 2 were formed by dissolving Compound Example 1, Comparative Compound 1 (disclosed in J. Am. Chem. Soc. 2010, 132, 8852-8853) or Comparative Compound 2 (disclosed in WO 2017/103610) in aerated or degassed octafluoropentanol.

TABLE 2

| Formulation | n-dopant precursor |
|---|---|
| Formulation Example 1 aerated | Compound Example 1 |
| Formulation Example 1 degassed | Compound Example 1 |
| Comparative Formulation 1 aerated | Comparative Compound 1 |
| Comparative Formulation 1 degassed | Comparative Compound 1 |
| Comparative Formulation 2 aerated | Comparative Compound 2 |
| Comparative Formulation 2 degassed | Comparative Compound 2 |

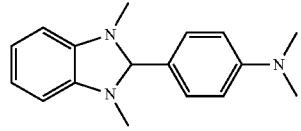

Comparative Compound 1

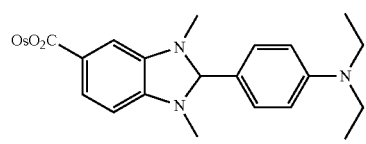

Comparative Compound 2

Octafluoropentanol was de-aerated by bubbling with nitrogen.

A mass spectrometer was used to measure the change in the m/z ratio of the compounds in the formulation over time.

Figure 2:
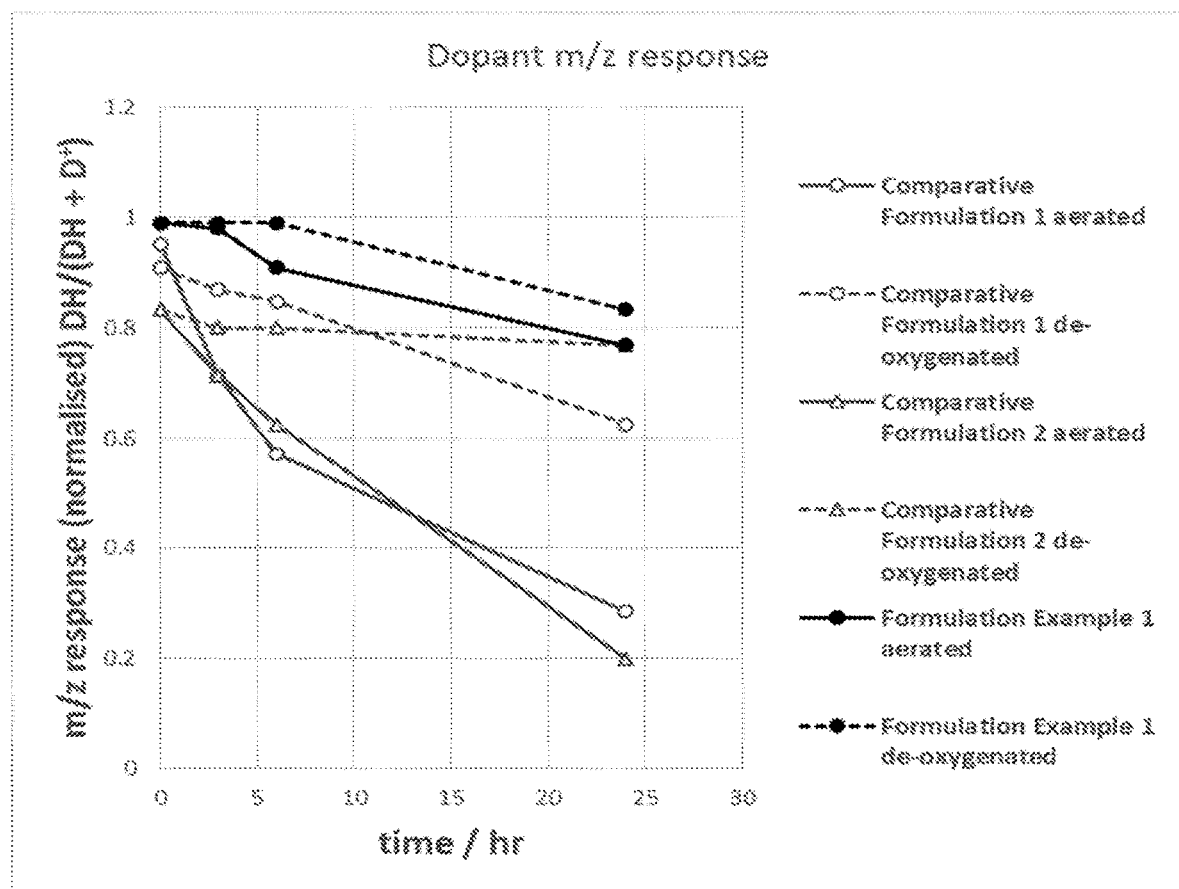
FIG. 2 is a graph of m/z response over time of a formulation containing a compound of formula (I) and comparative formulations.

With reference to FIG. 2, the m/z ratios of aerated Comparative Formulations 1 and 2 fall much faster than that of aerated Formulation Example 1.

Composition Example 1

Compound Example 1 was mixed with Acceptor Polymer 1 having the following repeat unit and the composition was heated:

Acceptor Polymer 1

Figure 3:
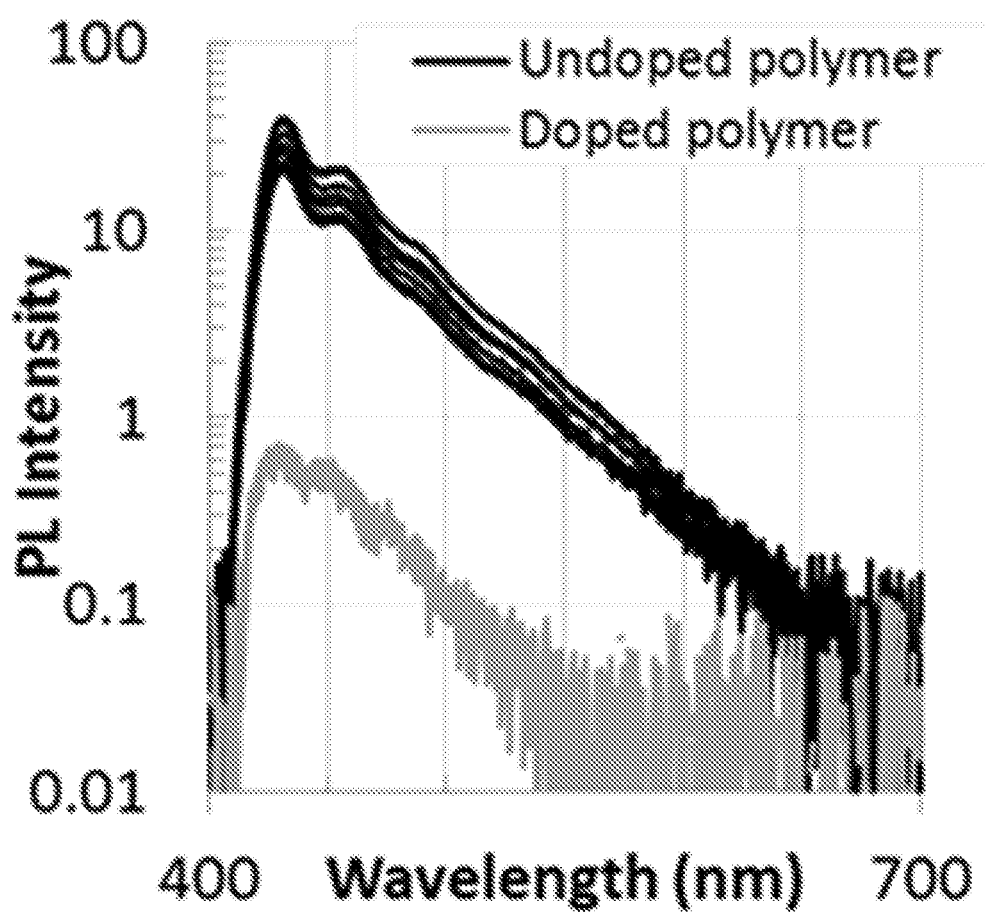
FIG. 3 is a graph of photoluminescent intensity for a composition according to an embodiment before and after activation of the composition.

With reference to FIG. 3, luminance of the composition following heating is much lower than that of the composition before heating, indicating quenching of luminescence as a result of doping upon heating of the composition. Measurements were made using a PL microscope with 365 nm excitation at a fixed intensity.

Device Example 1

An organic light-emitting having the following structure was formed:
ITO/HIL (20 nm)/HTL (20 nm)/LEL (90 nm)/EIL (10 nm)/Al (100 nm)/Ag (100 nm)
in which ITO is an indium tin oxide anode; HIL is a hole-injection layer; HTL is a hole-transporting layer; EIL is an electron injection layer and LEL is a light-emitting layer.

To form the device, a substrate carrying ITO was cleaned using UV/Ozone. The hole injection layer was formed by spin-coating an aqueous formulation of a hole-injection material available from Nissan Chemical Industries and heating the resultant layer. The hole-transporting layer was formed by spin-coating a hole-transporting polymer from xylene followed by heating to form a crosslinked hole-transporting layer. The light-emitting layer was formed by spin-coating a light-emitting material from xylene solution. The electron-injection layer was formed by spin-coating a formulation of Acceptor Polymer 2 and Compound Example 1 (50:50 by weight) from octafluoropentanol solution. After spin-coating the electron injection layer, the EIL was dried at 80° C. for 10 min, in a glovebox, followed by deposition of the cathode by thermal evaporation in vacuum.

The cathode was formed by evaporation of a first layer of aluminium and a second layer of silver.

The devices were then encapsulated and heated at 130° C. for 10 minutes.

The hole-transporting polymer is a crosslinkable polymer having fluorene and amine repeat units.

The light-emitting polymer is a blue fluorescent polymer containing fluorene and amine repeat units.

Acceptor Polymer 2 has the following structure:

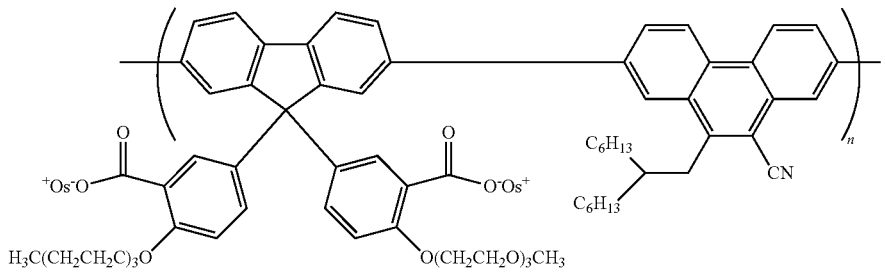

Acceptor Polymer 2 was formed by Suzuki polymerization as disclosed in WO00/53656 of 50 mol % each of the following monomers to form a precursor polymer followed by hydrolysis of the precursor polymer:

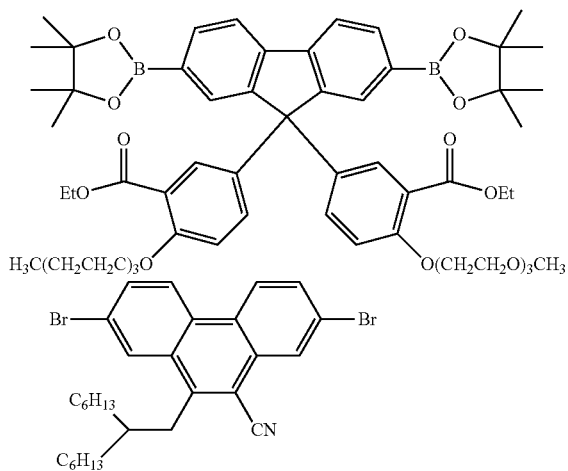

To hydrolyse the polymer, nitrogen was bubbled separately for 30 minutes in 113 ml of tetrahydrofuran, in 42 ml of methanol and in a solution of cesium hydroxide (0.80 g, 4.73 mmol) in 3.4 ml of water. 2.24 g of the precursor polymer was suspended in the tetrahydrofuran and heated up to 65° C. Mixture was stirred until full dissolution of the polymer. Methanol was added drop wise followed by the cesium hydroxide solution. Mixture was stirred at 65° C. for 16 hours and cooled down to room temperature. Solution was filtered and concentrated to 42 ml. It was precipitated into 800 ml of diethyl ether. The slurry was stirred for 10 minutes and filtered. Polymer was dried in vacuum oven at 50° C. overnight to yield 2.52 g of Acceptor Polymer 2, 96% yield.

Device Example 2

A device was prepared as described with reference to Device Example 1 except that the electron injection layer was formed to a thickness of 50 nm.

Figure 4:
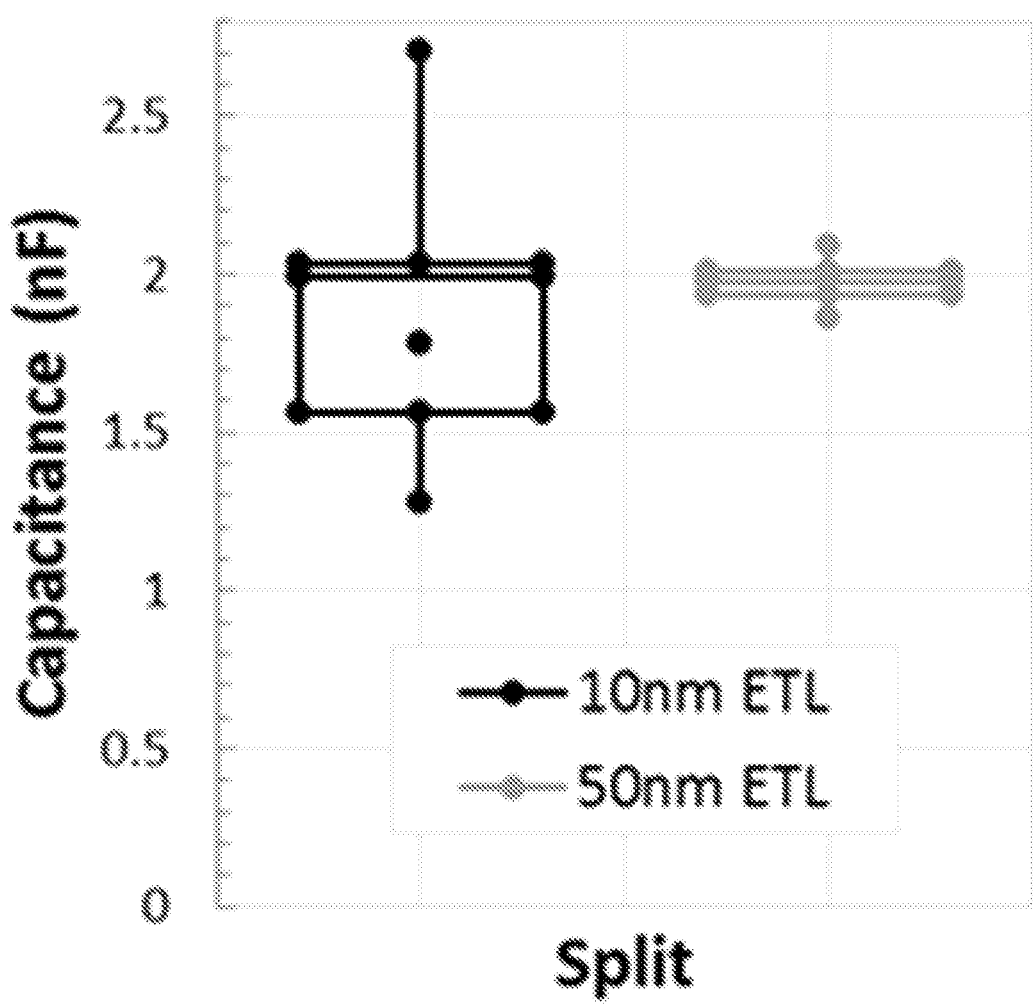
FIG. 4 is a graph of capacitances of organic light-emitting devices containing an electron-injection layer of different thicknesses.

With reference to FIG. 4, the capacitances of Device Examples 1 and 2 are similar, indicating that Electron Transporting Polymer 1 has been doped and is behaving as a conductor.

Square Wave Voltammetry

Measured HOMO, LUMO and SOMO levels of materials described herein are set out in Table 3.

TABLE 3

| Polymers | HOMO/eV vs vacuum | LUMO/eV vs vacuum |
|---|---|---|
| Acceptor Polymer 1 | −6.16 | −2.27 |
| Acceptor Polymer 2 | −5.95 | −2.54 |

| Dopants | Precursor HOMO/eV | Active SOMO/eV |
|---|---|---|
| Comparative Compound 1 | −4.70 | −2.57 |
| Comparative Compound 2 | −4.57 | −2.56 |
| Compound Example 1 | −4.68 | −2.50 |

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A compound of formula (I):

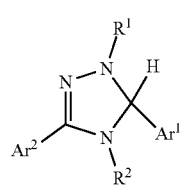

wherein $R^1$ and $R^2$ are each independently a linear, branched or cyclic $C_{1-20}$ alkyl group; and
$Ar^1$ and $Ar^2$ are each independently an aromatic or heteroaromatic group which is unsubstituted or substituted with one or more substituents.

2. A compound according to claim 1 wherein $Ar^1$ is a $C_{6-20}$ aromatic group.

3. A compound according to claim 2 wherein $Ar^1$ is phenyl.

4. A compound according to claim 1 wherein $Ar^2$ is a $C_{6-20}$ aromatic group.

5. A compound according to claim 4 wherein $Ar^2$ is phenyl.

6. A compound according to claim 1 wherein $Ar^1$ and $Ar^2$ are each independently unsubstituted or substituted with one or more substituents selected from the group consisting of:

branched, linear or cyclic $C_{1-12}$ alkyl wherein one or more non-adjacent, non-terminal C atoms of the $C_{1-12}$ alkyl group may be replaced with O, S, $NR^5$, C=O or COO wherein $R^5$ is a $C_{1-12}$ hydrocarbyl group; and ionic substituents.

7. A composition comprising an organic semiconductor and a compound according to claim 1.

8. A composition according to claim 7 wherein the organic semiconductor is a semiconducting polymer.

9. A composition according to claim 8 wherein the semiconducting polymer is a conjugated polymer.

10. A formulation comprising a compound according to claim 1 and at least one solvent.

11. A formulation according to claim 10 wherein the formulation further comprises an organic semiconductor.

12. A charge transfer salt formed by doping an organic semiconductor with an n-dopant formed from a compound of formula (I) according to claim 1.

13. A method of forming a charge-transfer salt, the method comprising:
    providing a composition comprising the compound according to claim 1 and an organic semiconductor; and
    activating the composition to cause n-doping of the organic semiconductor.

14. An organic electronic device comprising a layer comprising a charge-transfer salt according to claim 12.

15. An organic electronic device according to claim 14 wherein the organic electronic device is an organic light-emitting device comprising an anode, a cathode and a light-emitting layer between the anode and the cathode and wherein the layer comprising the charge-transfer salt is an electron injection layer between the light-emitting layer and the cathode.

16. An organic electronic device according to claim 15 wherein the electron injection layer is in contact with the light-emitting layer.

17. A method of forming a layer of an organic electronic device comprising the step of depositing a layer of a composition comprising a compound according to claim 1 and an organic semiconductor; and activating the composition to cause n-doping of the organic semiconductor.

18. A method according to claim 17 wherein the composition is activated by heating and/or irradiation.

19. A method according to claim 17 wherein the layer of the composition is deposited from a formulation.

* * * * *